United States Patent [19]
Dawson

[11] Patent Number: 5,467,377
[45] Date of Patent: Nov. 14, 1995

[54] COMPUTED TOMOGRAPHIC SCANNER

[76] Inventor: Ralph L. Dawson, 32975 NE. Polk St., Cambridge, Minn.

[21] Appl. No.: 228,110

[22] Filed: Apr. 15, 1994

[51] Int. Cl.$^6$ .................................................. H05G 1/60
[52] U.S. Cl. ........................................... 378/19; 378/4
[58] Field of Search .............................. 378/19, 4

[56] References Cited

U.S. PATENT DOCUMENTS

| | | | |
|---|---|---|---|
| 3,778,614 | 12/1973 | Hounsfield | 250/362 |
| 3,946,234 | 3/1976 | Hounsfield | 250/363 |
| 4,002,917 | 1/1977 | Mayo | 250/445 |
| 4,045,672 | 8/1977 | Watanabe | 250/360 |
| 4,220,863 | 9/1980 | McBride et al. | 250/445 |
| 4,239,972 | 12/1980 | Wagner | 250/445 |
| 4,315,157 | 2/1982 | Barnes | 250/445 |
| 4,352,021 | 9/1982 | Boyd et al. | 378/12 |
| 4,352,986 | 10/1982 | Pfeiler | 378/14 |
| 4,442,489 | 4/1984 | Wagner | 378/19 |
| 5,228,069 | 7/1993 | Arenson et al. | 378/19 |

FOREIGN PATENT DOCUMENTS

| | | |
|---|---|---|
| 0374289 | 6/1990 | Germany . |
| 1-280443 | 7/1978 | Japan . |

OTHER PUBLICATIONS

"Basic Computed Tomography Terminology", Technicare Corporation, Cleveland, Ohio, pp. 1–12.
"Principles of CT", Manual No. 961119, Revision B, Oct., 1985, Technicare, a Johnson & Johnson company.
Quantum System brochure, 961101, May, 1984, pp. 1–30.

*Primary Examiner*—Craig E. Church
*Attorney, Agent, or Firm*—Merchant, Gould, Smith, Edell, Welter & Schmidt

[57] ABSTRACT

A tomographic system in which an X-ray beam is deflected to sequential non-adjacent locations to collect imaging information.

1 Claim, 7 Drawing Sheets

COMPUTED TOMOGRAPHIC SCANNER

TECHNICAL FIELD

The present invention relates to a computed tomographic scanner for generating images of internal body organs and structures.

BACKGROUND

Computed tomographic scanners are well known in the art and have evolved over time. In general, they may be classified based upon their scanning technique and the geometric relationships between the X-ray source and the detectors.

Early scanners used a "translate-and-rotate" technique, where multiple independent pencil beams of X-rays emerged from a collimator and impinged on an array of detectors. In use, the X-ray tube and detector array are linked together and move as a single unit in a linear "translation direction". Next the entire assembly would be rotated a few degrees and translated again. The collection of scan data was very time consuming with this structure, due to the complex mechanical motion of the system.

Next "rotating-source/rotating-detector" systems were developed. In these systems the X-ray source and detector array are linked together and rotate about the patients body. More recently systems have been developed in which only the X-ray tube moves illuminating a large stationary array of detectors.

Each of these approaches involves compromises in terms of cost, complexity and scan time. In general it is desirable to complete a scan as rapidly as possible to reduce the deleterious effects of patient motion and to reduce the overall dosage of x-rays.

SUMMARY DISCLOSURE OF INVENTION

The computed tomographic scanner of the present invention includes an X-ray tube which may be rotated about a patient axis to a selected angular location (X,Y). The X-ray tube illuminates an array of stationary detectors located in a ring which is concentric with the patient axis.

The X-ray tube incorporates deflection structures which permit the X-ray beam to emerge from various apertures along a Z-axis. Thus X-ray tube can generate several sequential Z-axis slices of information at any given angular location, without physically moving.

A complimentary data acquisition architecture is provided to collect slice data developed by the system. This architecture preferably includes multiple segment detectors and a scan sequence that permits the rapid collection of data. In use, the X-ray tube is stepped to a fixed angular position in the X,Y plane then the X-ray beam is driven sequentially to illuminate the various stationary detectors. The illumination sequence permits detectors to become fully quiescent prior to re-illumination by the X-ray beam. This operational sequence permits the acquisition of several z-axis slices to be taken without moving the X-ray tube.

BRIEF DESCRIPTION OF THE DRAWINGS

An illustrative and exemplary computed tomographic scanner is shown in the accompanying drawings, wherein like reference numerals refer to identical structure throughout and in which.

DETAILED DESCRIPTION

Figure 1:
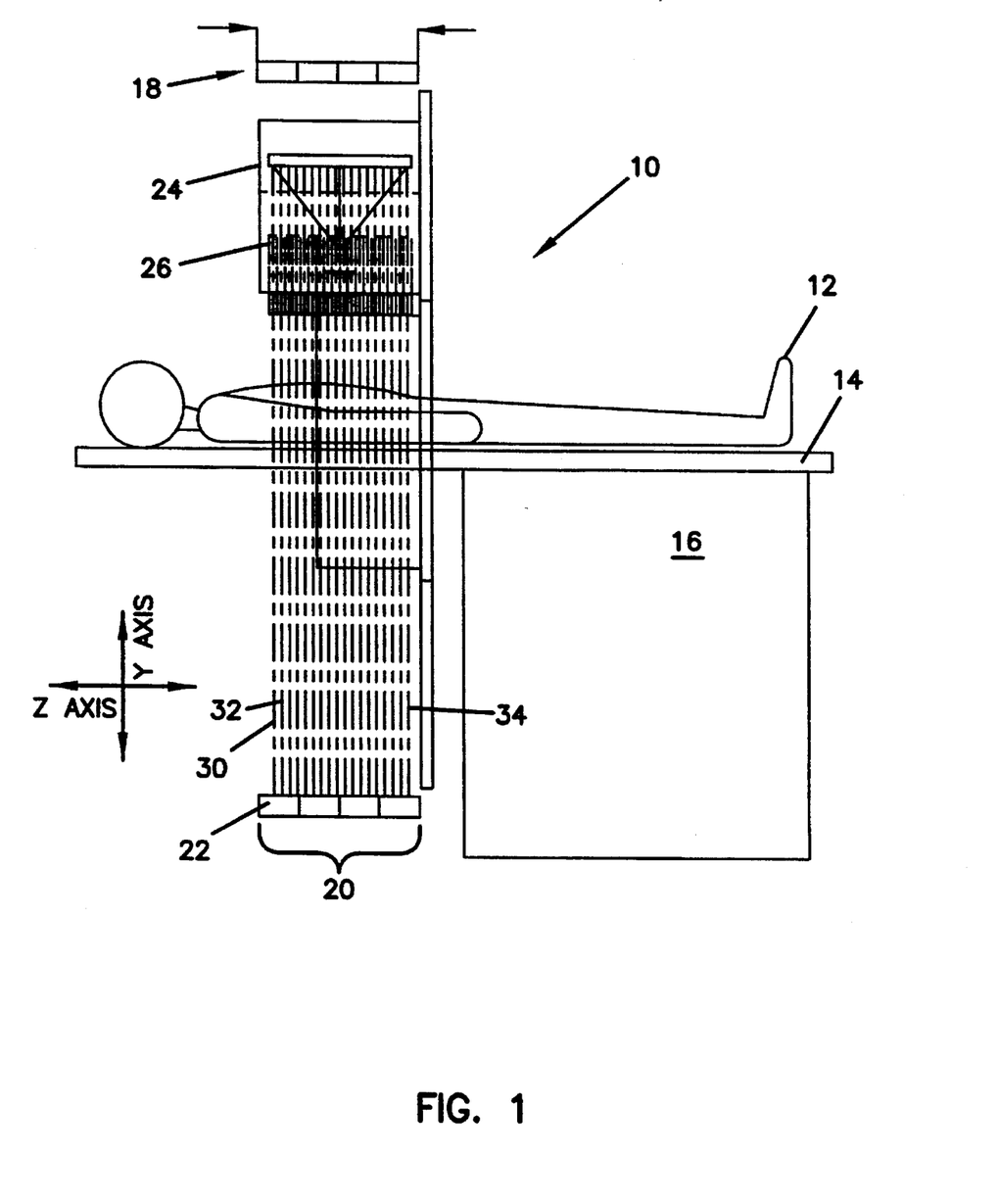
FIG. 1 is a cross-section of the computed tomographic scanner.

FIG. 1 is a schematic cross-sectional diagram which depicts a representative but not limiting embodiment of the computed tomographic scanner 10. The subject 12 is placed on a translation table 14 which can be incrementally moved in the Z direction to periodically reposition the subject 12. Table drive mechanisms are located within system cabinet 16.

A stationary detector ring 18 surrounds the subject 12 with the axis of the ring detector 18 parallel to the Z axis. The detector ring 18 is made up of a number of detector modules, typified by module 20. In the Z-axis direction each detector module 20, has several individual detector segments typified by detector segment 22.

Figure 2:
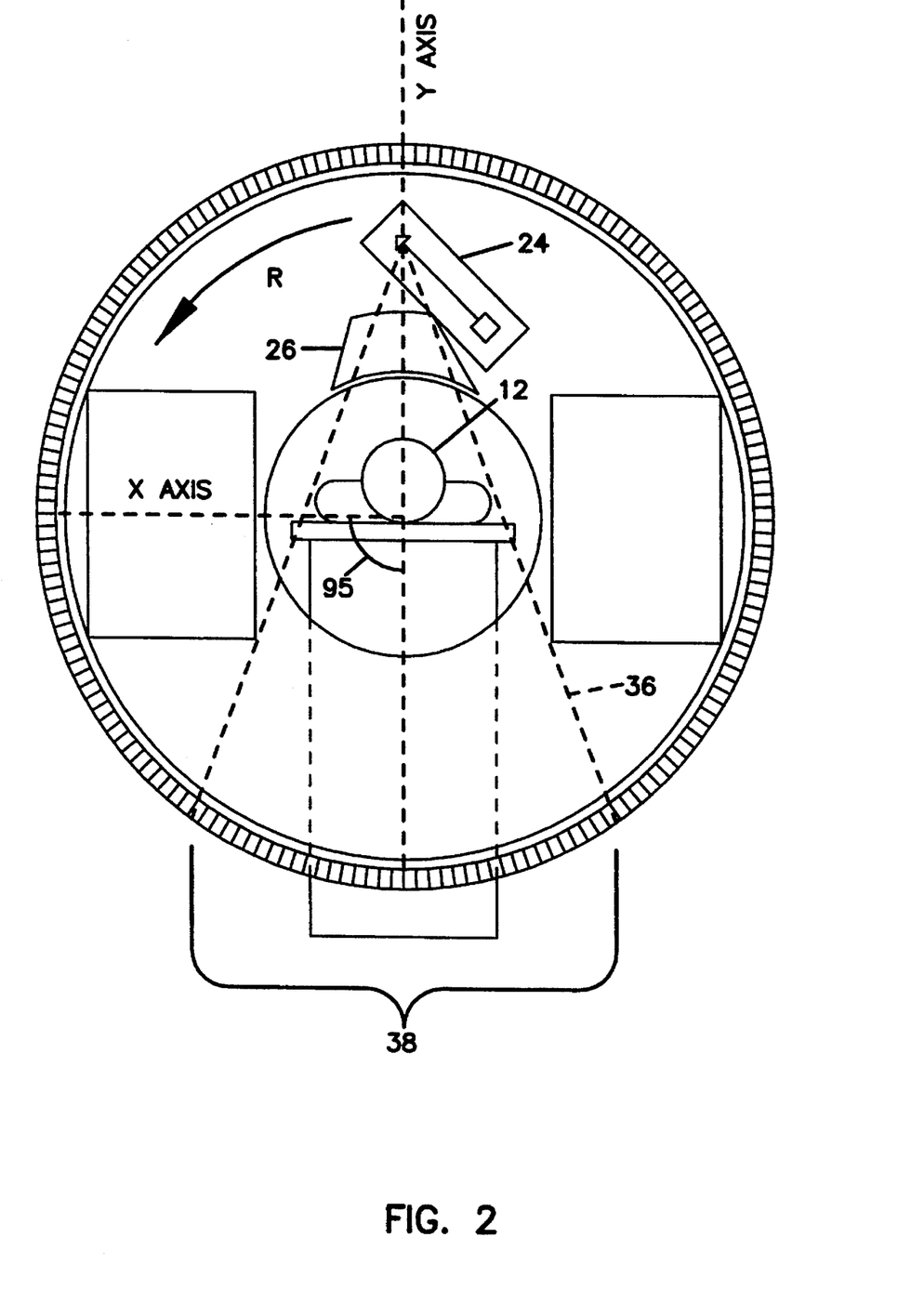
FIG. 2 is a cross-section of the computed tomographic scanner.

FIG. 2 is a schematic cross-sectional diagram which depicts the computed tomographic scanner 10. In this view the subject 12 is illuminated by the fan shaped X-ray beam 36.

The X-ray tube 24 and collimator 26 are coupled together and together they illuminate a portion of the subject's 12 body. In general, the X-ray tube 24 and collimator 26 may be moved together in the angular direction depicted by path arrow 42. This "angular" motion moves the X-ray source location and is required for tomographic analysis.

At any given angular location the x-ray tube is stationary. The X-ray beam emitted is moved to various positions along the Z axis electronically. Each of these Z-axis positions is referred to as a slice. In FIG. 1 multiple slices are depicted as typified by slice 30; slice 32; and slice 34. In FIG. 2 the fan shaped beam 36 illuminates a set of detector modules identified as detector set 38. These two views of the slice geometry show that multiple slices fall on a single detector crystal 22 as seen in FIG. 1, and a single slice 36 may fall on a number of detector crystals depicted as detector set 38 in FIG. 2. After the detector outputs are read for all z-axis slices the X-ray tube 24 and collimator 26 rotate in the R direction to establish a new data set. Multiple data sets are used to develop images of the interior of the subject, as is well known in this art.

Figure 3:
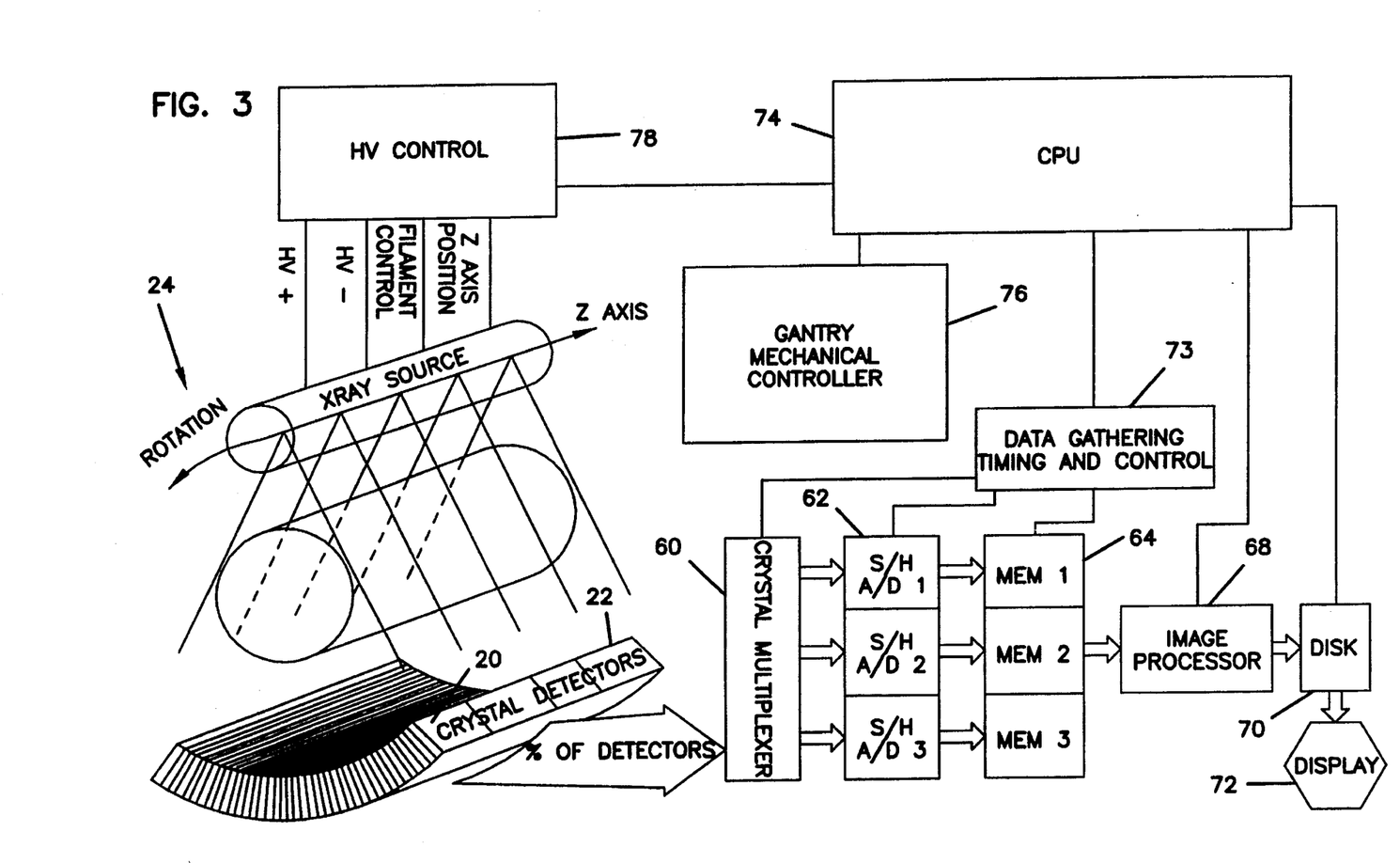
FIG. 3 is a system level schematic diagram of the computed tomographic scanner system.

FIG. 3 shows the overall system in a schematic form. The X-ray tube illuminates the body 12 at multiple Z-axis locations. The several detector segments convert the X-ray rays into light photons which are converted into electrical signals. The detectors outputs are selected by multiplexer 60 and sent to an array of sample and hold circuits and analog to digital converter circuits 62 which digitize the detectors signals. This digitized information is transferred to memory circuits 64. A conventional image processor 68 displays the computed image on a display 72 which is coupled to a hard disk 70 for information storage. The entire system is supervised and controlled by a computer 74 which generates mechanical gantry signals delivered to a gantry controller 76. The gantry controller 76 moves the X-ray tube 24. The computer also generates Z-axis location signals supplied to a high voltage control circuit 78. The high voltage control generates the deflection voltages to position the x-ray beam in the Z-axis. The computer 74 also generates timing and control signals which coordinate the collection of data from the crystals.

Figure 4:
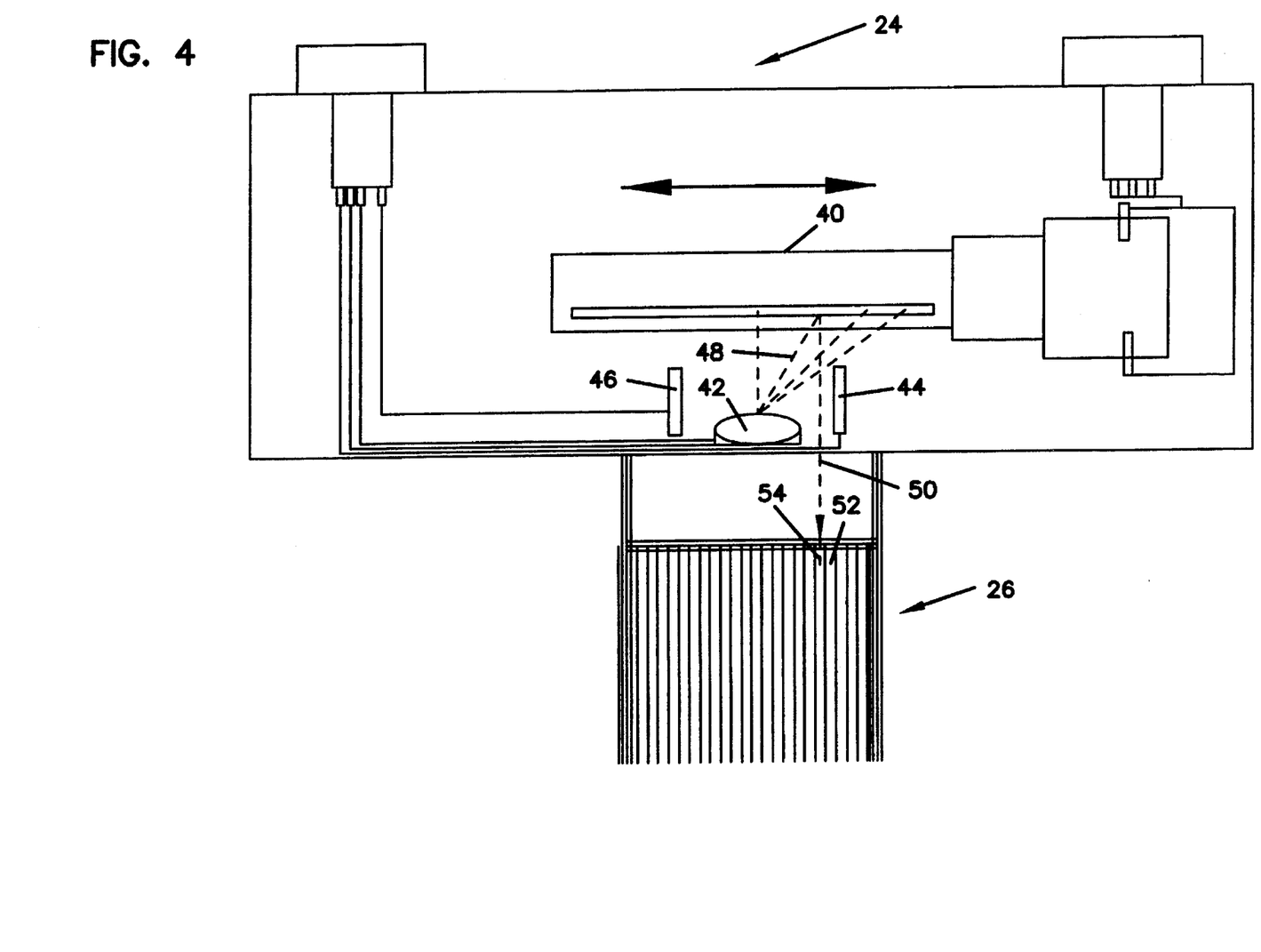
FIG. 4 is a cross-section of the X-ray tube of the computed tomographic scanner.

FIG. 4 shows the X-ray tube 24 in more detail. A rotating anode 40 is the target for electrons emitted by the cathode 42. The electron beam is deflected along the length of the anode 40 by a pair of electrostatic deflection plates shown a palate 44 and plate 46. The deflection of the electron beam 48 causes X-rays to be emitted at various locations along the length of the anode 40, typified by X-ray beam 50. Thus illuminating individual sections of the collimator 26. The parallel plates of the collimator typified by plate 52 and plate 54 define the Z-axis dimension of the slice. In practice a 2 mm slice is preferred for most anatomical imaging.

Figure 5:
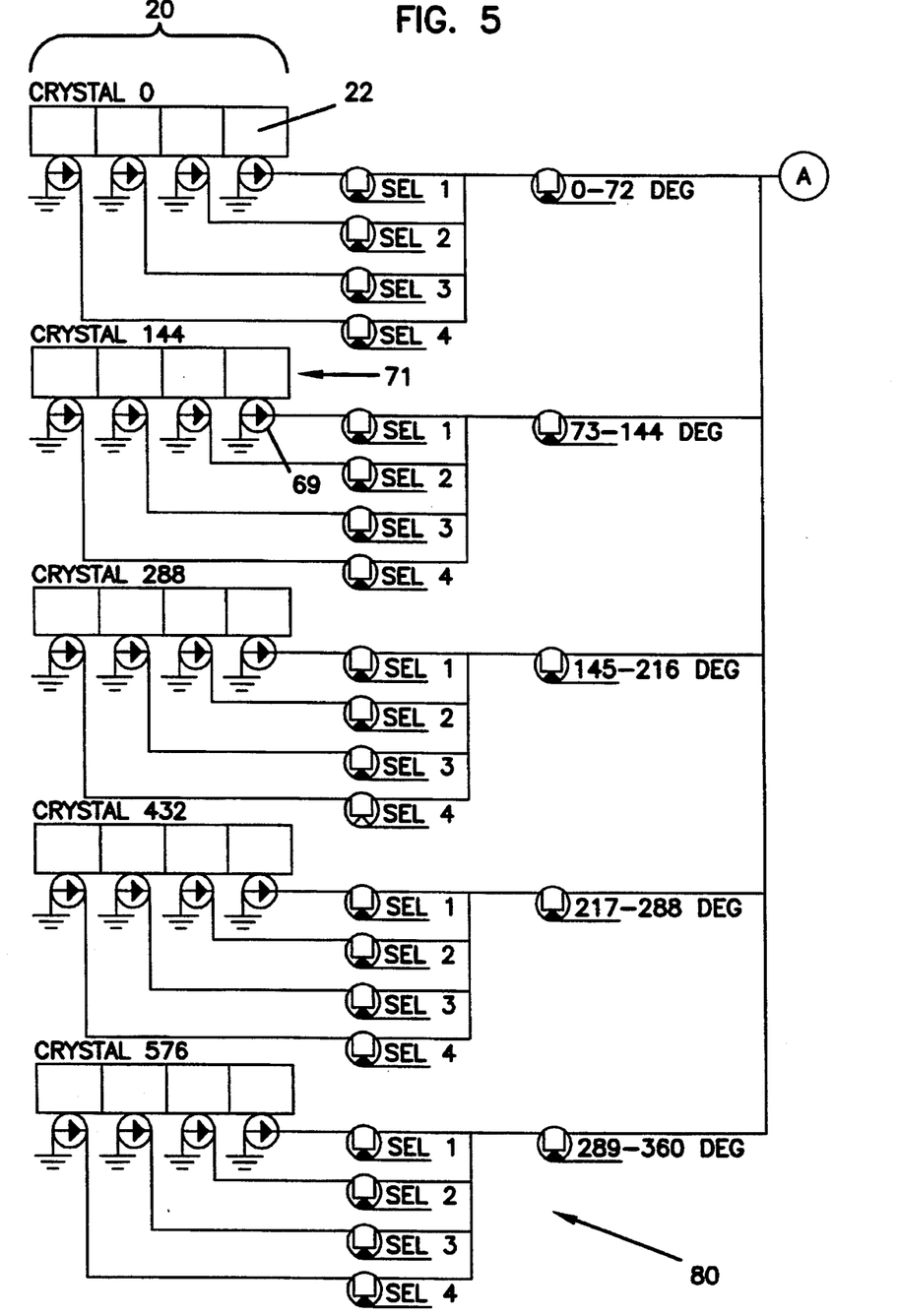
FIG. 5 and 5A are schematic diagrams for an exemplary data acquisition system for the computed tomographic scanner.
Figure 5A:
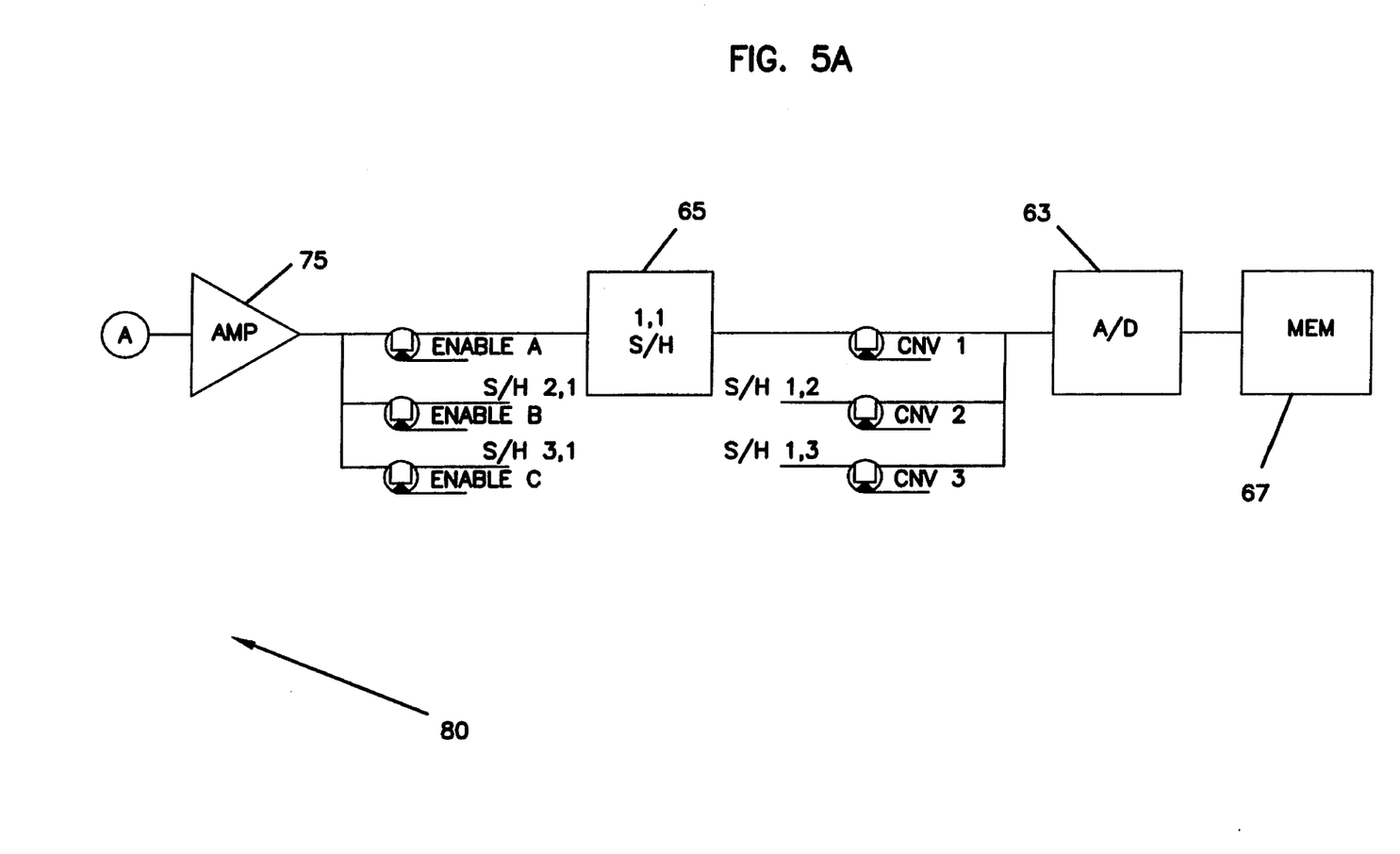
Figure 6:
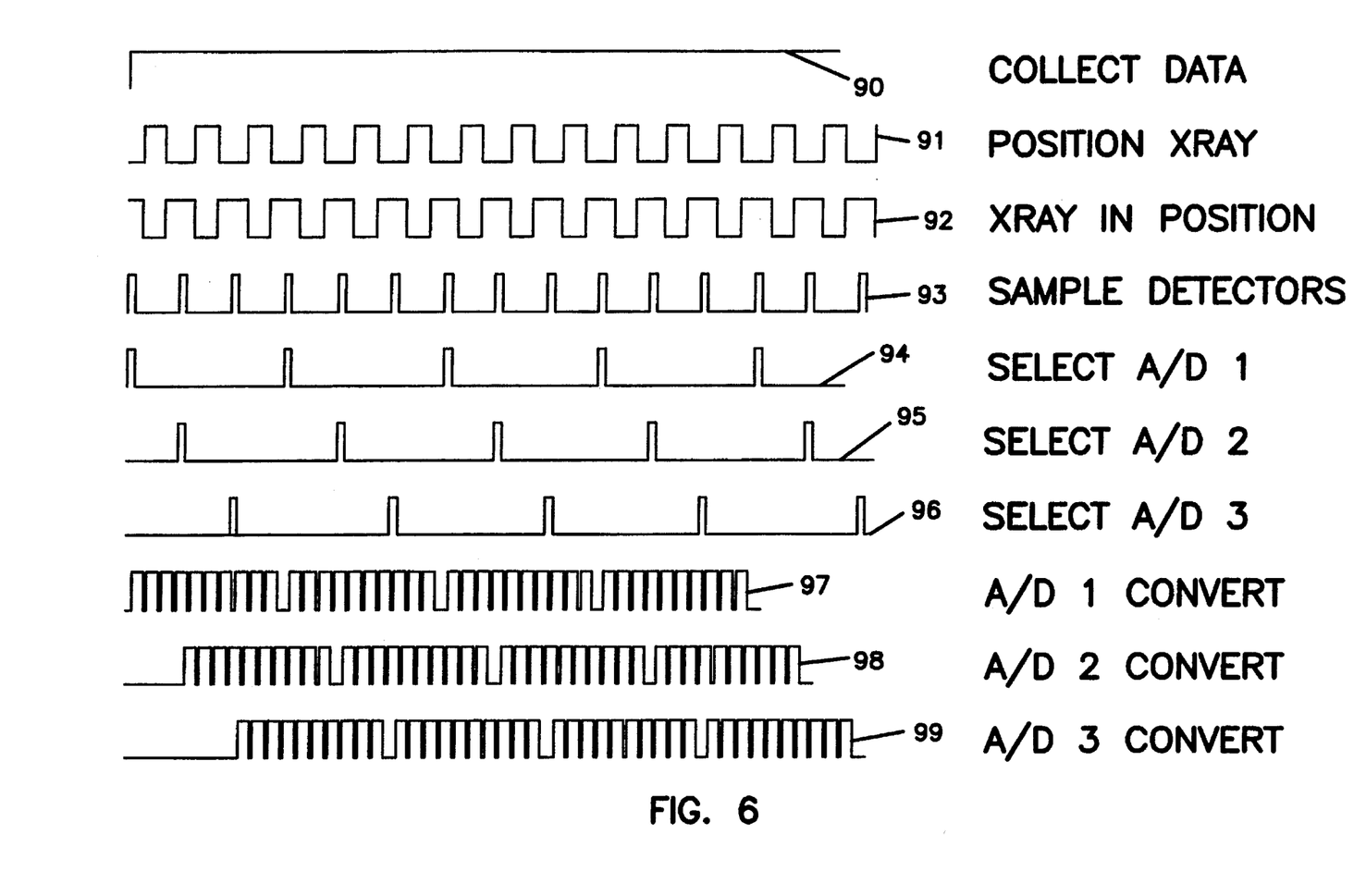
FIG. 6 is a timing diagram for an exemplary data acquisition system for the computed tomographic scanner.

Returning to FIG. 1 one can see that the detector segment 22 is substantially longer in the Z-axis direction than the slice 30. To maximize data collection speed it is preferred to move the X-ray beam to capture slice data from sequential detector segments rather than take slice data from adjacent slices. FIG. 5 and FIG. 6 taken together show an illustrative embodiment for circuitry form acquiring the sequential data.

FIG. 5 is schematic of the preferred signal channel 80 architecture. Each of the detector modules 20 includes several detector segments typified by crystal 20 and segment 22. The detector segments 22 are typically monolithic crystals 71 of Cesium Iodide or Cadmium Tungstate which convert incident X-rays into visible light photons. A photo diode 69 or other light detector is coupled to the detector crystal 71 to convert incident photons into an electrical current which is a function of the intensity of the X-rays falling on the crystal 71. Each detector module 20 may have a single signal conditioning amplifier 75 coupled to several sample and hold circuits typified by sample and hold circuit 65. Typically a single A to D converter 62; and memory 67 may be shared by several detector segments. Appropriate multiplexer signals are developed by the data controller 73 to select a single detector segment via transistor switches typified by transistor switch 74 during a discrete timing window. In operation, the output of each photo detector 69 is digitized and stored in memory 67.

The structures set forth permit the control means to selectively move the X-ray beam from one Z-axis location to another anywhere along the Z-axis. In this fashion the slice location in the z-axis is randomly addressable. This permits preferred method of operation to proceed as follows. First the X-ray tube 24 and associated collimator 26 is moved to a first angular position as represented in FIG. 2 by angle 95. Next the X-ray beam is moved to a slice location that illuminates one detector segment. Slice 32 as shown on FIG. 1 satisfies this requirement. Next the photo detector output associated with this slice is digitized and transferred to an appropriate memory location. Next the X-ray beam is directed to illuminate a non-adjacent detector segment. In FIG. 1 slice 34 meets this requirement. The ability to randomly address the detectors permits the detector crystal to become fully quiescent and permits sufficient time for the signal acquisition channel to return to nominal conditions before another slice is acquired. This sequence permits very rapid data acquisition which is limited by the repositioning characteristics of the X-ray tube and not by the recovery characteristics of the detector crystals. This technique also allows selection of detector crystals based upon their cost and quantum efficiently and not there extinction time characteristics.

FIG. 6 is a timing diagram which depicts an illustrative step-wise sequence for carrying out the method taught by the invention. Trace 90 depicts the data collection cycle. In trace 91 the X-ray beam is moved to a z-axis location and permitted to settle. This process may take 3 microseconds. In trace 92 the X-ray beam is in position and in trace 93 the detectors are sampled. Traces 94 95 and 96 depict differing conversion phases for separate detectors. The photo currents generated by these various detectors are held until the completion of A to D conversion as indicated by traces 97 98 and 99. The timing diagram shows how the sampling and conversion system can be partitioned to maximize the data collection speed.

Although an exemplary embodiment of the computed tomographic scanner is disclosed herein many possible variations are contemplated within the scope of the invention which is to be interpreted by the following claims.

What is claimed is:

1. A tomographic scanner comprising:

an x-ray tube generating z-axis X-ray beams, each X-ray beam at a z-axis location forming a slice;

a stationary array of detectors, each detector having several segments, each segment having a photo detector;

control means for sequentially moving said X-ray beam to non-adjacent z axis locations and for collection data from detector segments corresponding to each z-axis location.

* * * * *

UNITED STATES PATENT AND TRADEMARK OFFICE
CERTIFICATE OF CORRECTION

PATENT NO. : 5,467,377

DATED : November 14, 1995

INVENTOR(S) : Ralph L. Dawson

It is certified that error appears in the above-identified patent and that said Letters Patent is hereby corrected as shown below:

In column 1, line 50, please delete "complimentary", and insert therefor --complementary--

In column 3, line 13 after the word "shown", please delete "a", and insert therefor --as--

In column 3, line 14, before "44", please delete the word "palate", and insert therefor --plate--

In column 3, line 28, before the word "schematic", please insert --a--

Signed and Sealed this

Ninth Day of April, 1996

Attest:

BRUCE LEHMAN

Attesting Officer

Commissioner of Patents and Trademarks